(12) United States Patent
Zhu

(10) Patent No.: US 9,713,720 B2
(45) Date of Patent: *Jul. 25, 2017

(54) NEUROSTIMULATION SYSTEM WITH THREE-DIMENSIONAL LEAD MIGRATION DETECTION AND AUTOMATIC NEUROSTIMULATION CORRECTION

(71) Applicant: Boston Scientific Neuromodulation Corporation, Valencia, CA (US)

(72) Inventor: Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/805,979

(22) Filed: Jul. 22, 2015

(65) Prior Publication Data
US 2015/0321009 A1    Nov. 12, 2015

Related U.S. Application Data

(63) Continuation of application No. 14/098,380, filed on Dec. 5, 2013, now Pat. No. 9,089,705.
(Continued)

(51) Int. Cl.
*A61N 1/08* (2006.01)
*A61N 1/36* (2006.01)
(Continued)

(52) U.S. Cl.
CPC ........ *A61N 1/36139* (2013.01); *A61B 5/0538* (2013.01); *A61B 5/7221* (2013.01);
(Continued)

(58) Field of Classification Search
CPC ............ A61N 1/36139; A61N 1/36071; A61N 1/37235; A61N 1/36185; A61N 1/0551;
(Continued)

(56) References Cited

U.S. PATENT DOCUMENTS 6,516,227 B1   2/2003   Meadows et al.
6,895,280 B2   5/2005   Meadows et al.
(Continued)

OTHER PUBLICATIONS

"U.S. Appl. No. 14/098,380, Non Final Office Action mailed Dec. 15, 2014", 13 pgs.
(Continued)

*Primary Examiner* — Michael Carey
(74) *Attorney, Agent, or Firm* — Schwegman Lundberg & Woessner, P.A.

(57) ABSTRACT

A neurostimulation system configured for providing therapy to a patient, comprises at least one implantable neurostimulation lead configured for being implanted adjacent target tissue of the patient, and an implantable neurostimulator configured for delivering electrical stimulation energy to the implantable neurostimulation lead(s) in accordance with a set of stimulation parameters capable, and monitoring circuitry configured for taking at least one measurement indicative of a three-dimensional migration of the neurostimulation lead(s) from a baseline position. The neurostimulation system further comprises at least one controller/processor configured for determining whether the three-dimensional migration of the neurostimulation lead(s) from the baseline position has occurred based on the measurement(s), and, based on the determined three-dimensional migration, generating a new set of stimulation parameters, and reprogramming the implantable neurostimulator with the new set of stimulation parameters.

20 Claims, 5 Drawing Sheets

Related U.S. Application Data

(60) Provisional application No. 61/734,947, filed on Dec. 7, 2012.

(51) Int. Cl.
*A61N 1/372* (2006.01)
*A61N 1/05* (2006.01)
*A61B 5/00* (2006.01)
*A61B 5/053* (2006.01)

(52) U.S. Cl.
CPC ....... *A61N 1/0551* (2013.01); *A61N 1/36071* (2013.01); *A61N 1/37235* (2013.01); *A61B 5/0084* (2013.01); *A61N 1/36185* (2013.01)

(58) Field of Classification Search
CPC .... A61B 5/7221; A61B 5/0538; A61B 5/0084
USPC ................................. 607/46, 59, 60, 62, 117
See application file for complete search history.

(56) References Cited

U.S. PATENT DOCUMENTS

| | | | |
|---|---|---|---|
| 6,993,384 B2 | 1/2006 | Bradley et al. | |
| 7,317,948 B1 | 1/2008 | King et al. | |
| 7,650,184 B2 | 1/2010 | Walter | |
| 7,831,307 B1 | 11/2010 | Moffitt | |
| 8,019,439 B2 | 9/2011 | Kuzma et al. | |
| 8,233,992 B2 | 7/2012 | Zhu et al. | |
| 8,380,301 B2 | 2/2013 | Zhu | |
| 8,412,345 B2 | 4/2013 | Moffitt | |
| 9,089,705 B2 * | 7/2015 | Zhu | A61N 1/36139 |
| 2001/0053885 A1 * | 12/2001 | Gielen | A61M 5/14276 604/20 |
| 2006/0224222 A1 * | 10/2006 | Bradley | A61N 1/36071 607/116 |
| 2007/0168004 A1 | 7/2007 | Walter | |
| 2007/0168007 A1 | 7/2007 | Kuzma et al. | |
| 2009/0099624 A1 * | 4/2009 | Kokones | A61B 5/0476 607/59 |
| 2010/0137944 A1 | 6/2010 | Zhu | |
| 2010/0331922 A1 | 12/2010 | DiGiore et al. | |
| 2011/0054551 A1 | 3/2011 | Zhu et al. | |
| 2011/0106215 A1 | 5/2011 | Moffitt | |
| 2011/0257709 A1 * | 10/2011 | Ackermann | A61N 1/0551 607/62 |
| 2012/0239109 A1 | 9/2012 | Lee | |
| 2014/0163639 A1 | 6/2014 | Zhu | |

OTHER PUBLICATIONS

"U.S. Appl. No. 14/098,380, Notice of Allowance mailed Mar. 24, 2015", 7 pgs.

"U.S. Appl. No. 14/098,380, Response filed Mar. 3, 2015 to Non Final Office Action mailed Dec. 15, 2014", 16 pgs.

Barker, John Michael, et al., "Temporary Neurostimulation Lead Identification Device", File History of U.S. Appl. No. 61/030,506, (Feb. 21, 2008).

Cameron, T., "Safety and Efficacy of Spinal Cord Stimulation for the Treatment of Chronic Pain: a 20-Year Literature Review", J Neurosurg: Spine 2004, 100, (2004), 254-567.

* cited by examiner

NEUROSTIMULATION SYSTEM WITH THREE-DIMENSIONAL LEAD MIGRATION DETECTION AND AUTOMATIC NEUROSTIMULATION CORRECTION

RELATED APPLICATION DATA

The present application is a continuation of U.S. application Ser. No. 14/098,380, filed Dec. 5, 2013, now issued as U.S. Pat. No. 9,089,705, which claims the benefit under 35 U.S.C. §119 to U.S. provisional patent application Ser. No. 61/734,947, filed Dec. 7, 2012. The foregoing applications are hereby incorporated by reference into the present application in their entirety.

FIELD OF THE INVENTION

The present invention relates to tissue stimulation systems, and more particularly, to apparatus and methods for determining migration of neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, Functional Electrical Stimulation (FES) systems such as the Freehand system by NeuroControl (Cleveland, Ohio) have been applied to restore some functionality to paralyzed extremities in spinal cord injury patients. Furthermore, in recent investigations Peripheral Nerve Stimulation (PNS) systems have demonstrated efficacy in the treatment of chronic pain syndromes and incontinence, and a number of additional applications are currently under investigation. Occipital Nerve Stimulation (ONS), in which leads are implanted in the tissue over the occipital nerves, has shown promise as a treatment for various headaches, including migraine headaches, cluster headaches, and cervicogenic headaches.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. Thus, electrical pulses can be delivered from the neurostimulator to the stimulation leads to stimulate the tissue and provide the desired efficacious therapy to the patient. The neurostimulation system may further comprise a handheld patient programmer in the form of a remote control (RC) to remotely instruct the neurostimulator to generate electrical stimulation pulses in accordance with selected stimulation parameters. A typical stimulation parameter set may include the electrodes that are acting as anodes or cathodes, as well as the amplitude, duration, and rate of the stimulation pulses.

Thus, the RC can be used to instruct the neurostimulator to generate electrical stimulation pulses in accordance with the selected stimulation parameters. Typically, the stimulation parameters programmed into the neurostimulator can be adjusted by manipulating controls on the RC to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

The RC may, itself, be programmed by a clinician, for example, by using a clinician's programmer (CP), which typically includes a general purpose computer, such as a laptop, with a programming software package installed thereon. Typically, the RC can only control the neurostimulator in a limited manner (e.g., by only selecting a program or adjusting the pulse amplitude or pulse width), whereas the CP can be used to control all of the stimulation parameters, including which electrodes are cathodes or anodes.

In the context of an SCS procedure, one or more stimulation leads are introduced through the patient's back into the epidural space, such that the electrodes carried by the leads are arranged in a desired pattern and spacing to create an electrode array. One type of commercially available stimulation leads is a percutaneous lead, which comprises a cylindrical body with ring electrodes, and can be introduced into contact with the affected spinal tissue through a Touhy-like needle, which passes through the skin, between the desired vertebrae, and into the epidural space above the dura layer. After proper placement of the stimulation leads at the target area of the spinal cord, the leads are anchored in place at an exit site to prevent movement of the stimulation leads.

To facilitate the location of the neurostimulator away from the exit point of the stimulation leads, lead extensions are sometimes used. The stimulation leads, or the lead extensions, are then connected to the IPG, which can then be operated to generate electrical pulses that are delivered, through the electrodes, to the targeted tissue, and in particular, the dorsal column and dorsal root fibers within the spinal cord. The stimulation creates the sensation known as paresthesia, which can be characterized as an alternative sensation that replaces the pain signals sensed by the patient. Intra-operatively (i.e., during the surgical procedure), the neurostimulator may be operated to test the effect of stimulation and adjust the parameters of the stimulation for optimal pain relief. The patient may provide verbal feedback regarding the presence of paresthesia over the pain area, and based on this feedback, the lead positions may be adjusted and re-anchored if necessary. A computer program, such as Bionic Navigator®, available from Boston Scientific Neuromodulation Corporation, can be incorporated in a clinician's programmer (CP) (briefly discussed above) to facilitate selection of the stimulation parameters. Any incisions are then closed to fully implant the system. Post-operatively (i.e., after the surgical procedure has been completed), a clinician can adjust the stimulation parameters using the computerized programming system to re-optimize the therapy.

The efficacy of SCS is related to the ability to stimulate the spinal cord tissue corresponding to evoked paresthesia in the region of the body where the patient experiences pain. Thus, the working clinical paradigm is that achievement of an effective result from SCS depends on the neurostimulation lead or leads being placed in a location (both longitudinal, lateral, and depth) relative to the spinal tissue such that the electrical stimulation will induce paresthesia located in approximately the same place in the patient's body as the pain (i.e., the target of treatment). If a lead is not correctly positioned, it is possible that the patient will receive little or no benefit from an implanted SCS system. Thus, correct lead placement can mean the difference between effective and ineffective pain therapy, and as such, precise positioning of the leads proximal to the targets of stimulation is critical to the success of the therapy.

For example, multi-lead configurations, which enable more programming options for optimizing therapy, have been increasingly used in SCS applications. The use of multiple leads that are grouped together in close proximity to each other at one general region of the patient (e.g., side-by-side parallel leads along the spinal cord of the patient), increases the stimulation area and penetration depth (therefore coverage), as well as enables more combinations of anodic and cathodic electrodes for stimulation, such as transverse multipolar (bipolar, tripolar, or quadra-polar) stimulation, in addition to any longitudinal single lead configuration. Furthermore, with these lead configurations, current can be manipulated between leads medio-laterally to create the desired stimulation field. The resulting stimulation field is highly dependent on the relative position of the electrodes selected for stimulation.

Although the lead(s) may initially be correctly positioned relative to each other or relative to the stimulation target(s), the lead(s) are at risk of migration relative to each other and/or relative to the stimulation target(s). The lead(s) may migrate both acutely (e.g., during posture change or during activity/exercise) or chronically. In the context of SCS, the lead(s) may potentially migrate in three dimensions (rostro-caudally (along the spinal cord), medio-laterally (lateral to the spinal cord), and dorsal-ventrally (depth of the lead relative to the spinal cord). Notably, because the thickness of the cerebral spinal fluid (CSF) between the lead(s) and the spinal cord vary along the length spinal cord, migration of the lead(s) in the rostro-caudal direction may necessarily result in dorsal-ventral migration of the lead(s).

As a result, the therapy provided to the patient by the neurostimulation system may be compromised. Once this occurs, the patient may have to schedule another visit to the physician or clinician in order to adjust the stimulation parameters of the system by reprogramming the neurostimulator to compensate for the lead migration. Until the neurostimulator is reprogrammed, however, the patient will not be getting the quality of therapy previously provided by the neurostimulation system. Furthermore, before realizing that a visit to the physician or clinician is necessary, the patient may attempt to improve the compromised therapy by adjusting the stimulation energy delivered by the neurostimulation system via operation of the RC. However, not knowing that the lead migration is the reason for the compromised therapy, and given that the RC only has limited control over the neurostimulator (which typically allows only selection of programs and adjustment of pulse amplitude and pulse width), the patient will not be able to compensate for lead migration, which typically would require a modification in the electrodes that serve as cathodes/anodes—a skill a patient would typically not have.

When lead migration occurs, proper paresthesia coverage can most often be recaptured by reprogramming the IPG, e.g., by using the Bionic Navigator® software. When multiple percutaneous leads are used, programming of the IPG often requires the knowledge of the relative positions between the leads in order to properly place the poles of the generated electrical field. Such information, however, is not readily available to the programmer unless fluoroscopic imaging is performed. Fluoroscopic imaging involves ionized radiation, adds time and cost, and requires a bulky instrument, both of which may limit its use in the clinical setting, and effectively prevent its use outside of the clinical setting. Thus, lead migration continues to be the most common technical complication of spinal cord stimulation therapy. A literature review suggested the incident rate of lead migration was approximately 13.2% (see T. Cameron, *Safety and Efficacy of Spinal Cord Stimulation for the Treatment of Chronic Pain: a 20-Year Literature Review*, J Neurosurg: Spine 2004, 100: 254-267).

In addition to lead migration, the occurrence of faulty electrodes may also compromise neurostimulation therapy. In particular, in the case where one or more electrodes that have been programmed to deliver the neurostimulation therapy have failed, the resulting stimulation field will change due to the inability of the failed electrode(s) to contribute to the resulting stimulation field. In the same manner described above, with the same problems, the IPG may be reprogrammed to recapture proper paresthesia coverage.

There, thus, remains a technique that better addresses the needs of a user when an implanted stimulation lead has migrated in the patient or an electrode has failed.

SUMMARY OF THE INVENTION

In accordance with the present inventions, a neurostimulation system configured for providing therapy to a patient is provided. The neurostimulation system comprises at least one implantable neurostimulation lead configured for being implanted adjacent target tissue of the patient, and an implantable neurostimulator configured for delivering electrical stimulation energy to the implantable neurostimulation lead(s) in accordance with a current set of stimulation parameters.

The neurostimulation system further comprises monitoring circuitry configured for taking at least one measurement indicative of a three-dimensional migration of the neurostimulation lead(s) from a baseline position. In one embodiment, the neurostimulation lead(s) carries a plurality of electrodes, and the monitoring circuitry is configured for taking one of the measurement(s) by conveying an electrical signal between the electrodes, and measuring an electrical parameter (e.g., an impedance, a field potential, or an evoked potential) in response to the conveyance of the electrical signal. In another embodiment, the neurostimulation lead(s) carries one of an optical transducer and an ultrasound transducer, and the monitoring circuitry is configured for taking one of the measurement(s) by conveying one of an optical signal or an ultrasound signal from the respective one of the optical transducer and ultrasound transducer to the target tissue, and measuring a return signal in response to the conveyance of the optical signal or ultrasound signal. If the target tissue is a spinal cord, and the neurostimulation lead(s) comprises at least two neurostimulation leads, the measurement(s) may be indicative of a rostro-caudal migration and a medio-lateral migration between the neurostimulation leads, and a dorsal-ventral migration of the neurostimulation leads relative to the spinal cord.

The neurostimulation system further comprises at least one controller/processor configured for determining whether the three-dimensional migration of the neurostimulation lead(s) from the baseline position has occurred based on the measurement(s), and, based on the determined three-dimensional migration, generating a new set of stimulation parameters capable (which preferably mimics a baseline volume of activation relative to the target tissue created by the current set of stimulation parameters or the peak (virtual pole) distribution of the generated field), and reprogramming the implantable neurostimulator with the new set of stimulation parameters. In one embodiment, the controller/processor(s) is configured for reprogramming the implantable stimulator with the new set of stimulation parameters by defining a virtual multipole relative to the target tissue, and computing fractionalized amplitude values for the electrodes carried by the neurostimulation lead(s) that emulate the virtual multipole, in which case, the new set of stimulation parameters will include the computed fractionalized amplitude values.

If the neurostimulation lead(s) comprises at least two neurostimulation leads, and one of the measurement(s) is indicative of a migration of the neurostimulation leads relative to each other, the controller/processor(s) may be configured for determining whether the migration of the neurostimulation lead(s) relative to each other has occurred based on the one measurement. If another one of the measurement(s) is indicative of a migration of the neurostimulation leads relative to the target tissue, the controller/processor(s) is configured for determining whether the migration of the neurostimulation leads relative to the target tissue has occurred based on the other measurement.

The neurostimulation system may further comprise memory configured for storing the baseline position of the neurostimulation lead(s), and the controller/processor(s) is configured for determining a magnitude of the three-dimensional migration of the neurostimulation lead(s) from the baseline position by determining a current three-dimensional position of the neurostimulation lead(s), comparing the current three-dimensional position of the neurostimulation lead(s) to the baseline position of the neurostimulation lead(s) to determine the magnitude.

The memory may also be configured for storing at least one threshold value, in which case, the controller/processor(s) may be configured for comparing the determined magnitude of the three-dimensional migration to threshold value(s), and reprogramming the implantable neurostimulator with the new set of stimulation parameters based on the comparison. In one embodiment, the controller/processor(s) is configured for automatically reprogramming the implantable neurostimulator with the new set of stimulation parameters when the determined magnitude of the three-dimensional migration exceeds any of the threshold value(s). In another embodiment, the neurostimulation system further comprises an external control device configured for receiving input from a user, for generating an alert signal when the determined magnitude of the three-dimensional migration exceeds the any threshold value, and for reprogramming the implantable neurostimulator with the new set of stimulation parameters in response to the user input. The controller/processor(s) may instruct the implantable neurostimulator to deliver electrical stimulation energy to the implantable neurostimulation lead(s) in accordance with the new set of stimulation parameters prior to reprogramming the implantable neurostimulator with the new set of stimulation parameters, in which case, the external control device may allow a user to prompt the controller/processor(s) to reprogram the implantable neurostimulator with the new set of stimulation parameters.

In an optional embodiment, the neurostimulation lead(s) carries a plurality of electrodes, the monitoring circuitry is further configured for taking at least another measurement indicative of coupling efficiencies between the electrodes and the tissue, and the controller/processor(s) is configured for determining whether any of the electrodes has a degraded coupling efficiency based on the other measurement(s), and, if any of the electrodes are determined to have a degraded coupling efficiency, automatically generating another new set of stimulation parameters, and reprogramming the implantable neurostimulator with the other new set of stimulation parameters.

In one embodiment, the monitoring circuitry is contained in the implantable neurostimulator. In another embodiment, the neurostimulation device further comprises an external control device containing the controller/processor(s). Alternatively, the controller/processor(s) may be contained in the implantable neurostimulator. If more than one controller/processor is used to perform the aforementioned functions, the controller/processor(s) may be distributed between the external control device and the implantable neurostimulator.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a multi-lead system such as a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
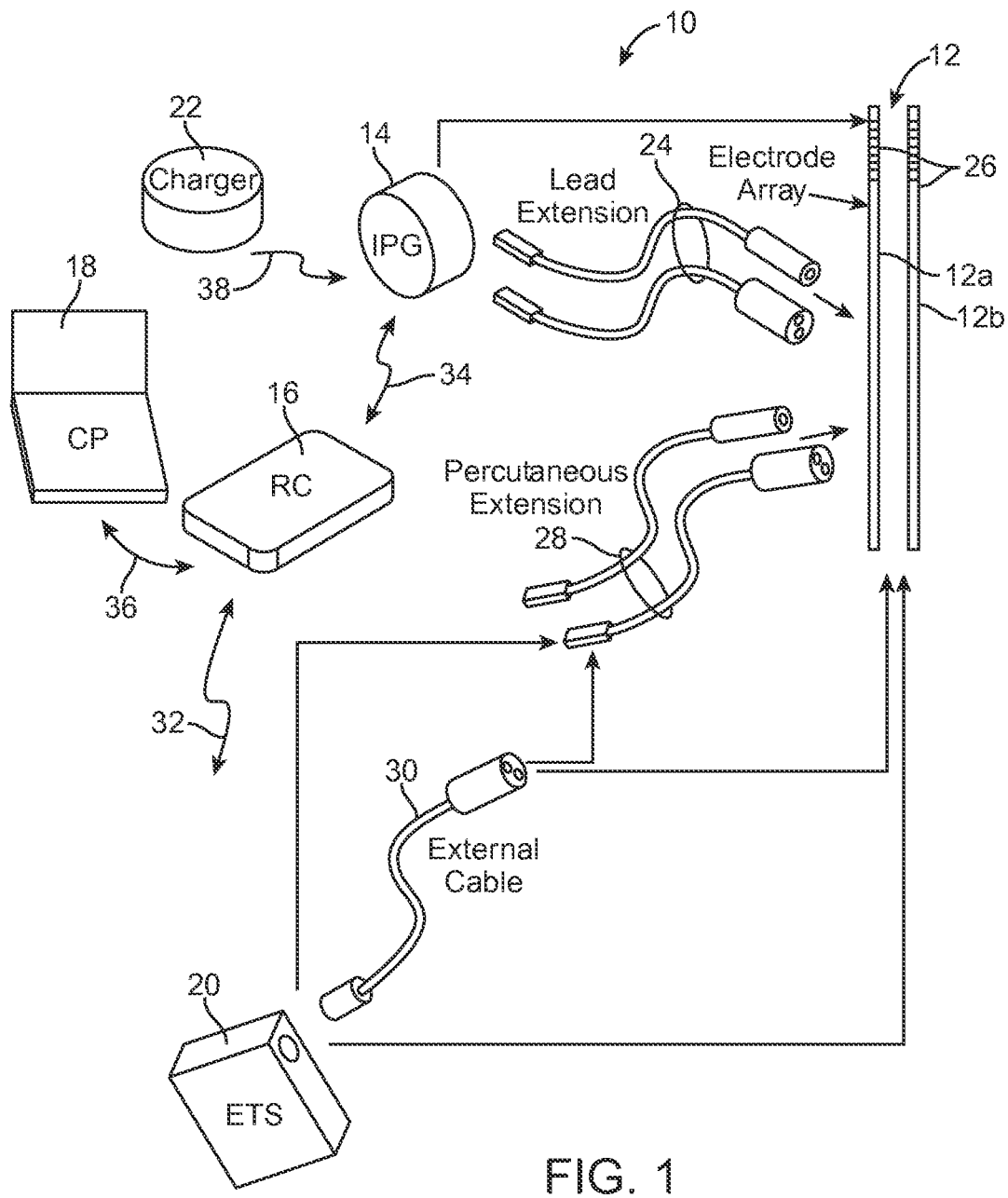
FIG. 1 is plan view of one embodiment of a spinal cord stimulation (SCS) system arranged in accordance with the present inventions.

Turning first to FIG. 1, an exemplary SCS system 10 generally comprises a plurality of neurostimulation leads 12 (in this case, two percutaneous leads 12(1) and 12(2)), an implantable pulse generator (IPG) 14, an external remote control (RC) 16, a Clinician's Programmer (CP) 18, an External Trial Stimulator (ETS) 20, and an external charger 22.

The IPG 14 is physically connected via two lead extensions 24 to the neurostimulation leads 12, which carry a plurality of electrodes 26 arranged in an array. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters. The IPG 14 and neurostimulation leads 12 can be provided as an implantable neurostimulation kit, along with, e.g., a hollow needle, a stylet, a tunneling tool, and a tunneling straw. Further details discussing implantable kits are disclosed in U.S. Application Ser. No. 61/030,506, entitled "Temporary Neurostimulation Lead Identification Device," which is expressly incorporated herein by reference.

The ETS 20 may also be physically connected via percutaneous lead extensions 28 or external cable 30 to the neurostimulation lead 12. The ETS 20, which has similar pulse generation circuitry as the IPG 14, also delivers electrical stimulation energy in the form of a pulse electrical waveform to the electrode array 26 in accordance with a set of stimulation parameters. The major difference between the ETS 20 and the IPG 14 is that the ETS 20 is a non-implantable device that is used on a trial basis after the neurostimulation lead 12 has been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation lead 12 is implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the CP 18, ETS 20, external charger 22 will not be described herein. Details of exemplary embodiments of these components are disclosed in U.S. Pat. No. 6,895,280, which is expressly incorporated herein by reference.

Figure 2:
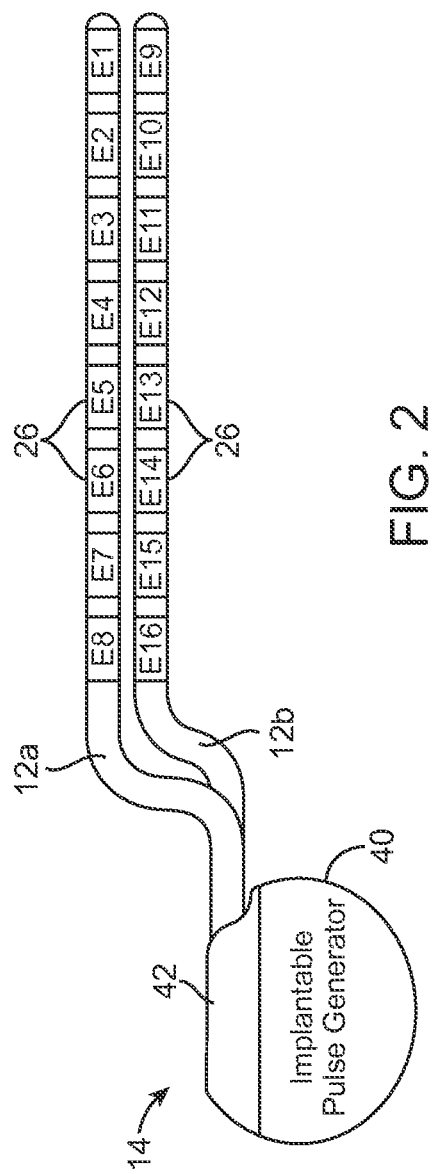
FIG. 2 is a plan view of an implantable pulse generator (IPG) and two neurostimulation leads used in the SCS system of FIG. 1.

Referring now to FIG. 2, the external features of the neurostimulation leads 12a, 12b and the IPG 14 will be briefly described. Each of the neurostimulation leads 12 has eight electrodes 26 (respectively labeled E1-E8 for the lead 12a and E9-E16 for the lead 12b). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 comprises an outer case 40 for housing the electronic and other components (described in further detail below). The outer case 40 is composed of an electrically conductive, biocompatible material, such as titanium, and forms a hermetically sealed compartment wherein the internal electronics are protected from the body tissue and fluids. In some cases, the outer case 40 may serve as an electrode. The IPG 14 further comprises a connector 42 to which the proximal ends of the neurostimulation leads 12 mate in a manner that electrically couples the electrodes 26 to the internal electronics (described in further detail below) within the outer case 40. To this end, the connector 42 includes two ports (not shown) for receiving the proximal ends of the three percutaneous leads 12. In the case where the lead extensions 24 are used, the ports may instead receive the proximal ends of such lead extensions 24.

As briefly discussed above, the IPG 14 includes pulse generation circuitry that provides electrical stimulation energy to the electrodes 26 in accordance with a set of parameters. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

With respect to the pulse patterns provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 40, so that the electrical current has a path from the energy source contained within the IPG case 40 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 40 of the IPG 14, so that electrical energy is transmitted between the selected electrode 26 and case 40. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

Figure 3:
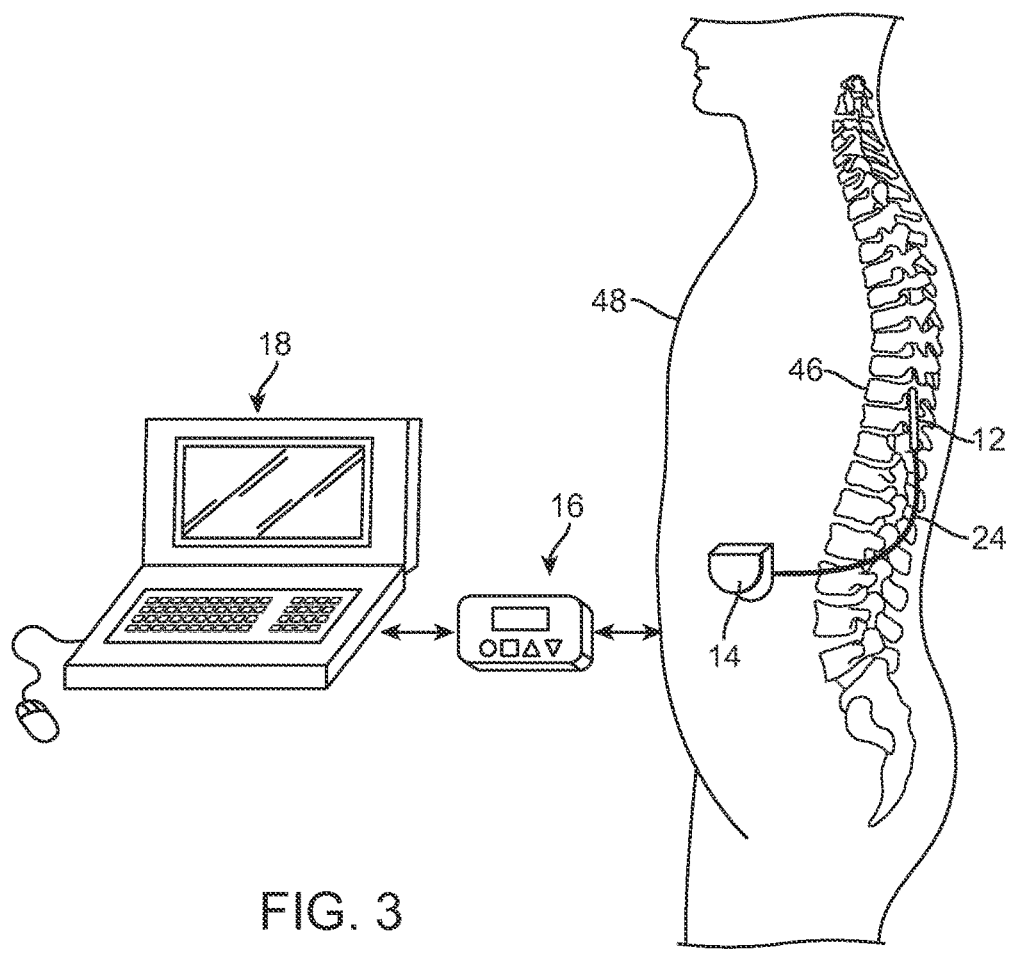
FIG. 3 is a plan view of the SCS system of FIG. 1 in use with a patient.

Referring to FIG. 3, the neurostimulation leads 12 are implanted at an initial position within the spinal column 46 of a patient 48. The preferred placement of the neurostimulation leads 12 is adjacent, i.e., resting near, or upon the dura, adjacent to the spinal cord area to be stimulated. Due to the lack of space near the location where the neurostimulation leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the neurostimulation leads 12. As there shown, the CP 18 communicates with the IPG 14 via the RC 16. After implantation, the IPG 14 can be operated to generate a volume of activation relative to the target tissue to be treated, thereby providing the therapeutic stimulation under control of the patient. As previously mentioned in the background of the invention, either or both of the neurostimulation leads 12 may inadvertently migrate from their initially implanted position, either relative to each other or relative to a point in the tissue of the patient 46, resulting in a change in the shape and/or location of the volume of activation relative to the target tissue.

Figure 4:
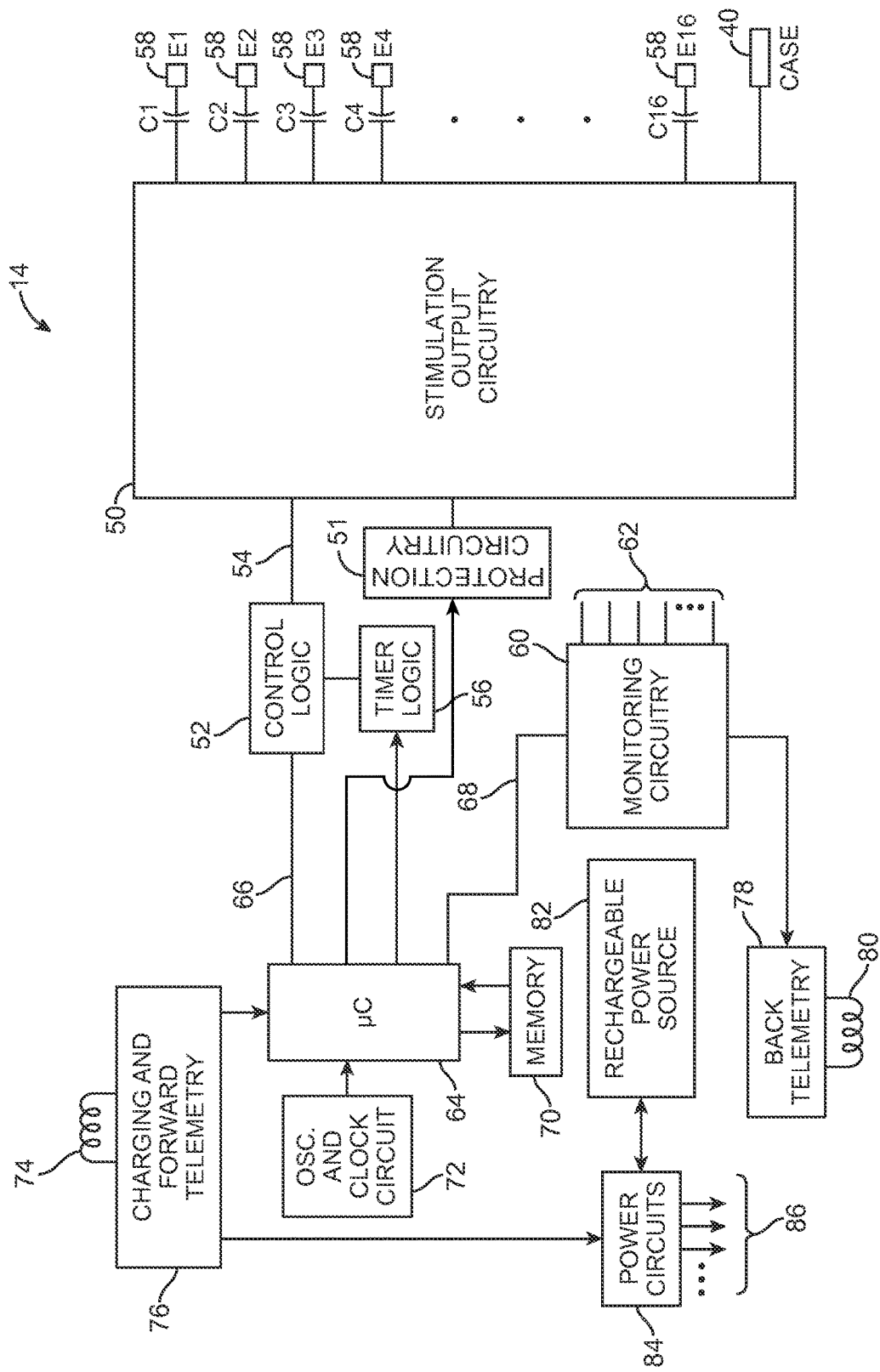
FIG. 4 is a block diagram of the internal components of the IPG of FIG. 1.

Turning next to FIG. 4, the main internal components of the IPG 14 will now be described. The IPG 14 includes stimulation output circuitry 50 configured for generating electrical stimulation energy in accordance with a defined pulsed waveform having a specified pulse amplitude, pulse rate, pulse width, pulse shape, and burst rate under control of control logic 52 over data bus 54. Control of the pulse rate and pulse width of the electrical waveform is facilitated by timer logic circuitry 56, which may have a suitable resolution, e.g., 10 μs. The stimulation energy generated by the stimulation output circuitry 50 is output via capacitors C1-C16 to electrical terminals 58 corresponding to the electrodes 26.

The stimulation output circuitry 50 may either comprise independently controlled current sources for providing stimulation pulses of a specified and known amperage to or from the electrical terminals 58, or independently controlled voltage sources for providing stimulation pulses of a specified and known voltage at the electrical terminals 58 or to multiplexed current or voltage sources that are then connected to the electrical terminals 58. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 60 for monitoring the status of various nodes or other points 62 throughout the IPG 14, e.g., power supply voltages, temperature, battery voltage, and the like. Notably, the electrodes 26 fit snugly within the epidural space of the spinal column, and because the tissue is conductive, electrical measurements can be taken from the electrodes 26. Significantly, the monitoring circuitry 60 is configured for taking such electrical measurements, so that, as will be described in further detail below, the positioning of each of the leads 12 relative to a reference point (e.g., the tissue and/or the other lead 12) may be determined. In the illustrated embodiment, the electrical measurements taken by the monitoring circuitry 60 for the purpose of determining the positioning of the leads 12 may be any suitable measurement, e.g., an electrical impedance, an electrical field potential, or an evoked potential. The monitoring circuitry 60 may also measure impedance at each electrode 26 in order to determine whether the coupling efficiency between the respective electrode 26 and the tissue has degraded (e.g., the coupling efficiency varies significantly during a certain period or the respective electrode is defective with respect to the connection between the electrode and the stimulation output circuitry 60 of the IPG 14 (e.g., it has an open circuit).

Electrical data can be measured using any one of a variety means. For example, the electrical data measurements can be made on a sampled basis during a portion of the time while the electrical stimulus pulse is being applied to the tissue, or immediately subsequent to stimulation, as described in U.S. patent application Ser. No. 10/364,436, which has previously been incorporated herein by reference. Alternatively, the electrical data measurements can be made independently of the electrical stimulation pulses, such as described in U.S. Pat. Nos. 6,516,227 and 6,993,384, which are expressly incorporated herein by reference.

To facilitate determination of the positioning of each neurostimulation lead 12, electrical signals can be transmitted between electrodes carried by one of the neurostimulation lead 12 and one or more other electrodes (e.g., electrodes on the same neurostimulation lead 12, electrodes on the other neurostimulation lead 12, the case 40 of the IPG 12, or an electrode affixed to the target tissue), and then electrical parameters can be measured in response to the transmission of the electrical signals.

For example, an impedance measurement technique may be performed by measuring impedance vectors, which can be defined as impedance values measured between selected pairs of electrodes 26. The interelectrode impedance may be determined in various ways. For example, a known current (in the case where the IPG 14 is sourcing current) can be applied between a pair of electrodes 26, a voltage between the electrodes 26 can be measured, and an impedance between the electrodes 26 can be calculated as a ratio of the measured voltage to known current. Or a known voltage (in the case where the IPG is sourcing voltage) can be applied between a pair of electrodes 26, a current between the electrodes 26 can be measured, and an impedance between the electrodes 26 can be calculated as a ratio of the known voltage to measured current.

As another example, a field potential measurement technique may be performed by generating an electrical field at selected ones of the electrodes 26 and recording the electrical field at other selected ones of the lead electrodes 26. This may be accomplished in one of a variety of manners. For example, an electrical field may be generated conveying electrical energy to a selected one of the electrodes 26 and returning the electrical energy at the IPG case. Alternatively, multipolar configurations (e.g., bipolar or tripolar) may be created between the lead electrodes 26. Or, an electrode that is sutured (or otherwise permanently or temporarily attached (e.g., an adhesive or gel-based electrode) anywhere on the patient's body may be used in place of the case IPG outer case or lead electrodes 26. In either case, while a selected one of the electrodes 26 is activated to generate the electrical field, a selected one of the electrodes 26 (different from the activated electrode) is operated to record the voltage potential of the electrical field.

As still another example, an evoked potential measurement technique may be performed by generating an electrical field at one of the electrodes 26, which is strong enough to depolarize the neurons adjacent the stimulating electrode beyond a threshold level, thereby inducing the firing of action potentials (APs) that propagate along the neural fibers. Such stimulation is preferably supra-threshold, but not uncomfortable. A suitable stimulation pulse for this purpose is, for example, 4 mA for 200 μs. While a selected one of the electrodes 26 is activated to generate the electrical field, a selected one or ones of the electrodes 26 (different from the activated electrode) is operated to record a measurable deviation in the voltage caused by the evoked potential due to the stimulation pulse at the stimulating electrode.

Alternatively, lead position can be monitored using other means, such as strain gauge elements or optical fibers/coherence sensors within the leads 12. In one embodiment, the neurostimulation leads 12 may carry optical or ultrasound transducers capable of transmitting optical or ultrasound signals into the target tissue (in this case, the spinal cord) and receiving the reflected optical or ultrasound signals reflected from the target tissue, so that the position of the neurostimulation leads 12 can be determined relative to the target tissue.

Significantly, the monitoring circuitry 60 takes measurements indicative of a three-dimensional migration of the neurostimulation leads 12 from a baseline position. These measurements may be taken periodically (e.g., one an hour). In the illustrated embodiment, the measurements are indicative of a rostro-caudal migration (along the spinal cord) and a medio-lateral migration (transverse to the spinal cord) of the neurostimulation leads 12 relative to each other (i.e., migration of the neurostimulation leads 12 relative to each other in two dimensions along a plane), and further indicative of a dorsal-ventral migration (depth primary due to CSF thickness) of the of the neurostimulation leads 12 relative to the spinal cord (i.e., migration of the neurostimulation leads 12 relative to the spinal cord in the remaining third dimension perpendicular to the plane). The three dimensional measurements may be taken using any variation or combination of the impedance, field potential, and evoked potential measurement techniques described above.

For example, for the relative rostro-caudal migration (lead stagger), electrical measurements can be taken in accordance with the techniques disclosed in U.S. Pat. No. 6,993,384, entitled "Apparatus and Method for Determining the Relative Position and Orientation of Neurostimulation Leads," U.S. Pat. No. 7,831,307, entitled "System and Method for Computationally Determining Migration of Neurostimulation Leads," and U.S. patent application Ser. No. 12/550,136, entitled "Method and Apparatus for Determining Relative Positioning Between Neurostimulation Leads," which are expressly incorporated herein by reference. For the relative medio-lateral migration (lateral lead separation), electrical measurements can be taken in accordance with the technique disclosed in U.S. patent application Ser. No. 12/623,976, entitled "Method and Apparatus for Determining Relative Positioning Between Neurostimulation Leads," which is expressly incorporated herein by reference. For the relative dorsal-ventral migration (lead depth), electrical or other types of measurements can be taken in accordance with the techniques disclosed in U.S. patent application Ser. No. 11/096,483, entitled "Apparatus and Methods for Detecting Migration of Neurostimulation Leads," and U.S. patent application Ser. No. 12/495,442, entitled "System and Method for Compensating for Shifting of Neurostimulation Leads in a Patent," which are expressly incorporated herein by reference. Optical interferometer techniques or ultrasound distance measuring techniques can alternatively be used to measure the relative dorsal-ventral lead migration.

The IPG 14 further comprises processing circuitry in the form of a microcontroller 64 that controls the control logic 52 over data bus 66, and obtains status data from the monitoring circuitry 60 via data bus 68. The microcontroller 64 additionally controls the timer logic 56. The IPG 14 further comprises memory 70 for storing stimulation programs and associated stimulation parameters, and an oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and stimulation parameters. In controlling the operation of the IPG 14, the microcontroller 64 is able to individually generate electrical pulses at the electrodes 26 using the stimulation output circuitry 50, in combination with the control logic 52 and timer logic 56, thereby allowing each electrode 26 to be paired or grouped with other electrodes 26, including the monopolar case electrode, and to control the polarity, amplitude, rate, and pulse width through which the current stimulus pulses are provided.

The IPG 14 further comprises an alternating current (AC) receiving coil 74 for receiving programming data (e.g., the operating program and/or stimulation parameters) from the RC 16 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further comprises back telemetry circuitry 78 and an alternating current (AC) transmission coil 80 for sending informational data (including the lead migration and electrode coupling efficiency data) sensed through the monitoring circuitry 60 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 82 and power circuits 84 for providing the operating power to the IPG 14. The rechargeable power source 82 may, e.g., comprise a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits) received by the AC receiving coil 74. To recharge the power source 82, an external charger (not shown), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

It should be noted that the diagram of FIG. 4 is functional only, and is not intended to be limiting. Those of skill in the art, given the descriptions presented herein, should be able to readily fashion numerous types of IPG circuits, or equivalent circuits, that carry out the functions indicated and described. It should be noted that rather than an IPG for the neurostimulator, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
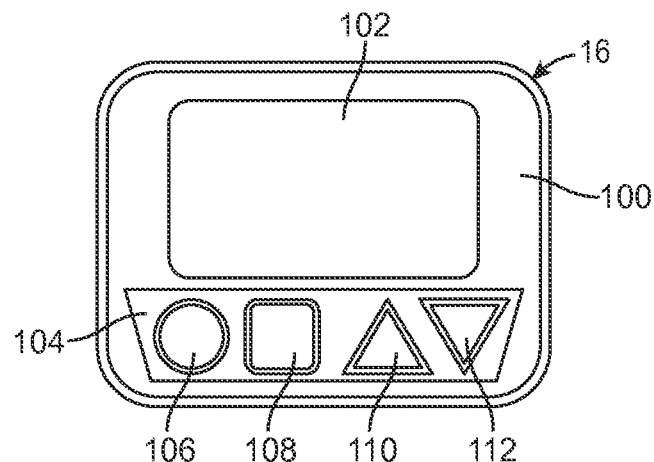
FIG. 5 is a plan view of a remote control that can be used in the SCS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), a lighted display screen 102, an audio transducer (speaker) 103, and a control pad 104 carried by the exterior of the casing 100. In the illustrated embodiment, the display screen 102 is a lighted flat panel display screen, and the control pad 104 comprises a membrane switch with metal domes positioned over a flex circuit, and a keypad connector connected directly to a PCB. In an optional embodiment, the display screen 102 has touchscreen capabilities. The control pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 16 to switch between screen displays and/or parameters. The buttons 110 and 112 serve as up/down buttons that can be actuated to increase or decrease any of stimulation parameters of the pulse generated by the IPG 14, including pulse amplitude, pulse width, and pulse rate.

Figure 6:
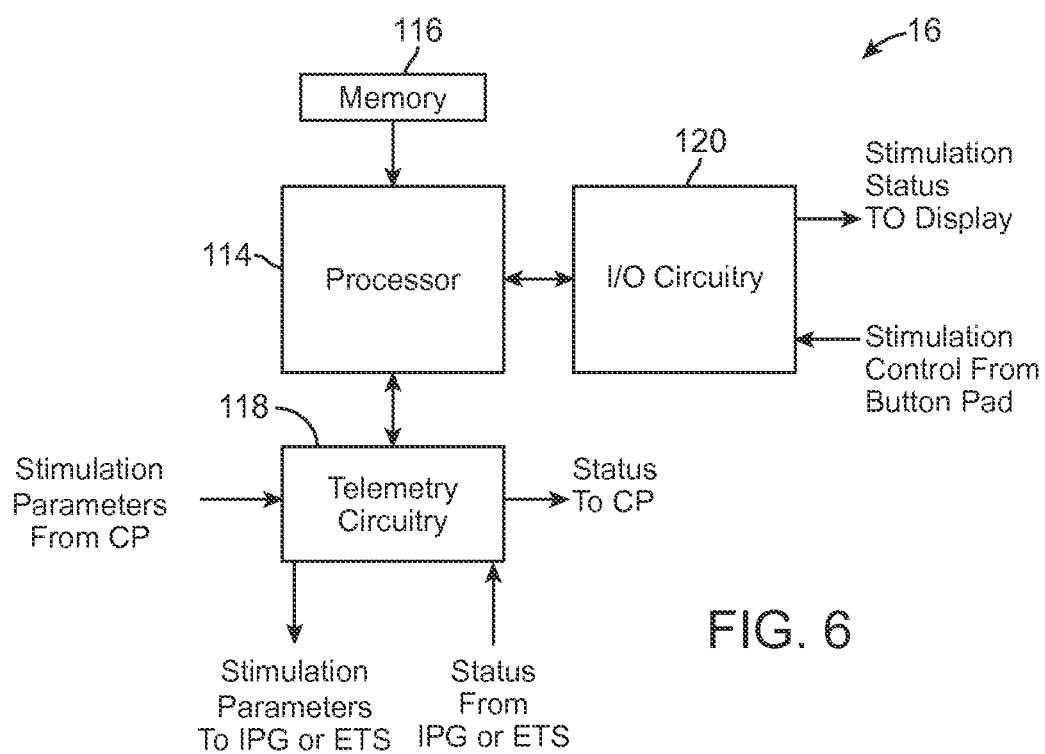
FIG. 6 is a block diagram of the internal componentry of the remote control of FIG. 5.

Referring to FIG. 6, the internal components of an exemplary RC 16 will now be described. The RC 16 generally includes a controller/processor 114 (e.g., a microcontroller), memory 116 that stores an operating program for execution by the controller/processor 114, and telemetry circuitry 118 for transmitting control data (including stimulation parameters and requests to provide status information) to the IPG 14 and receiving status information (including the measured electrical data) from the IPG 14 via link 34 (or link 32) (shown in FIG. 1), as well as receiving the control data from the CP 18 and transmitting the status data to the CP 18 via link 36 (shown in FIG. 1). The RC 16 further includes input/output circuitry 120 for receiving stimulation control signals from the control pad 104 and transmitting operational status information to the display screen 102 and speaker 103 (shown in FIG. 5). Notably, while the controller/processor 80 is shown in FIG. 5 as a single device, the processing functions and controlling functions can be performed by a separate controller and processor. Thus, it can be appreciated that the controlling functions described below as being performed by the RC 16 can be performed by a controller, and the processing functions described below as being performed by the RC 16 can be performed by a processor. Further details of the functionality and internal componentry of the RC 16 are disclosed in U.S. Pat. No. 6,895,280, which has previously been incorporated herein by reference.

Significantly, the controller/processor 114 is configured for invoking an auto-programming function that seeks correction in the case of significant lead migration in any of the three dimensions and/or significant coupling inefficiency of any of the electrodes 26.

To determine whether three-dimensional lead migration has occurred, the controller/processor 114 first determines in three dimensions whether the neurostimulation leads 12 have migrated from a baseline position based on the lead migration measurements taken by the monitoring circuitry 60 of the IPG 14. As discussed above, the lead position (whether it be the current position or the baseline position) is relative to a reference point, which can be, e.g., a point in the tissue of the patient, such that the absolute migration of respective neurostimulation lead 12 is determined, or can be, e.g., the position of the other neurostimulation lead 12, such that the migration of the respective neurostimulation lead 12 relative to each other is determined. In the illustrated embodiment, the relevant lead position is both relative to the other lead (rostro-caudal and medio-lateral lead migration relative to each other) and absolute (dorsal-ventral lead migration relative to the spinal cord).

Preferably, the baseline position is the position at which the migrated neurostimulation leads 12 were in when the IPG 14 was initially programmed (e.g., the position that the neurostimulation leads 12 were initially implanted when the patient was initially fitted with the system 10) or reprogrammed (e.g., the position that the neurostimulation leads 12 were in when the patient subsequently returned to the clinician's office for adjustment of the stimulation parameters). That is, the baseline position is preferably the position of the neurostimulation leads 12 that is optimum for the stimulation parameters currently programmed into the IPG 14 and/or RC 16.

To determine whether any migration of the neurostimulation leads 12 is significant enough to invoke the auto-programming function, the controller/processor 114 determines the magnitude at which each neurostimulation lead 12 has migrated from its baseline position in all three dimensions. In one embodiment, the controller/processor 114 accomplishes this function by determining a current three-dimensional position of the implanted neurostimulation lead 12 and computing a difference between the current position and the baseline position. As discussed above with respect to FIG. 4, the current position of the neurostimulation leads 12 can be determined from the lead migration measurements taken acquired from the monitoring circuitry 60 of the IPG 14.

After the magnitude or magnitudes at which each neurostimulation lead 12 has migrated from its baseline position is determined in the three dimensions, the controller/processor 114 compares the determined magnitude(s) to one or more threshold values representing an acceptable lead position tolerance. The threshold value(s) are stored in the memory 116. In one embodiment, a single magnitude of the lead migration is represented by a function (e.g., average or sum) of the magnitude components of the lead migration in all three dimensions. In this case, the controller/processor 114 may compare the resulting lead migration magnitude to a single threshold value. In another embodiment, the controller/processor 114 simply compares the magnitude components of the lead migration in all three dimensions can be respectively compared to three threshold values. In either case, if the determined magnitude(s) exceeds any of the corresponding threshold value(s), the controller/processor 114 invokes the auto-programming function.

In addition to determining three-dimensional lead migration, the controller/processor 114 is also configured for determining whether any of the electrodes 26 has a degraded coupling efficiency based on the electrode coupling efficiency measurements taken by the monitoring circuitry 60 of the IPG 14, and, if any of the electrodes 26 is determined to have a degraded coupling efficiency, generating the new set of stimulation parameters, and reprogramming the IPG 14 with the new set of stimulation parameters.

To determine whether coupling inefficiency in any of the electrodes 26 is significant enough to invoke the auto-programming function, the controller/processor 114 first determines which of the electrodes 26 is activated (i.e., which of the electrodes 26 are programmed to deliver the electrical stimulation energy) under the premise that any electrodes 26 that are not activated, even if found to have a significant coupling inefficiency, need not be corrected. The controller/processor 114 then compares each coupling efficiency measurement taken by the monitoring circuitry 60 of the IPG 14 for the activated electrodes 26 to a threshold value representing an acceptable electrode coupling efficiency. This coupling efficiency threshold value is stored, along with the lead migration threshold value(s), in the memory 116. In the illustrated embodiment, the coupling efficiency measurements takes the form of electrode impedances, which inversely vary with the coupling efficiency (i.e., the coupling efficiency decreases with an increasing electrode impedance). Thus, if the measured coupling efficiency for any activated electrode 26 is greater than the coupling efficiency threshold value, the controller/processor 114 invokes the auto-programming function. In this case, where the coupling efficiency measurements are vary with the coupling efficiency (i.e., the coupling efficiency decreases with a decreasing value of the measurement), if the measured coupling efficiency for any activated electrode 26 is less than the coupling efficiency threshold value, the controller/processor 114 invokes the auto-programming function.

Upon invoking the auto-programming function, whether based on significant lead migration or significant electrode coupling inefficiency, the controller/processor 114 may generate a new set of stimulation parameters capable of generating a volume of activation having a shape and location relative to the target tissue that most closely mimics the shape and location of the baseline volume of activation relative to the target tissue, and reprogramming the IPG 14 with the new set of stimulation parameters. In general, because fractionalized values for the electrodes 26 will primary effect the shape and location of the volume of activation, as opposed to other electrical parameters, such as pulse rate and pulse frequency, the new set of stimulation parameters will contain only new fractionalized current values.

To more efficiency and effectively mimic the baseline volume of activation relative to the target tissue, ideal virtual multipoles (e.g., an ideal bipole or ideal tripole) may be utilized. In particular, an ideal stimulation target in the form of an ideal virtual multipole, which can be assumed to define the shape and location of the baseline volume of activation relative to the spinal cord, can be stored in the memory 116 of the RC 16. The fractionalized amplitude values that emulate the ideal virtual multipole may be initially computed for the electrodes 26 by the RC 16 or the CP 18, and included within the set of stimulation parameters with which the IPG 14 is initially programmed, as described in U.S. patent application Ser. No. 12/938,282, entitled "System and Method for Mapping Arbitrary Electric Fields to Pre-existing Lead Electrodes," and U.S. patent application Ser. No. 13/420,060, entitled "Neurostimulation System for Defining a Generalized Virtual Multipole," which are incorporated herein by reference. The global amplitude value of the electrical stimulation energy, which can be assumed to define the size of the baseline volume of activation, may also be included within the set of stimulation parameters with which the IPG 14 is initially programmed, and stored with the ideal virtual multipole, in the memory 116 of the RC 16.

Upon a determination that the auto-programming function is to be invoked based on the occurrence of a significant rostro-caudal or medio-lateral migration of the neurostimulation leads 12 or the occurrence of a coupling inefficiency for an activated electrode, the controller/processor 114 may recall the ideal virtual multipole from the memory 116, and computes the fractionalized amplitude values for the electrodes 26 that emulate the recalled ideal virtual multipole, and includes these values in the new set of stimulation parameters used to reprogram the IPG 14. In the case where significant rostro-caudal or medio-lateral migration of the neurostimulation leads 12 is determined, the controller/processor 114 will taken into account the new rostro-caudal position and/or new medio-lateral position of the neurostimulation leads 12 relative to each other when computing the fractionalized amplitude values for the electrodes 26. In the case where an electrode 26 is determined to be inefficiency, the controller/processor 114 will exclude this inefficient electrode 26 when computing the fractionalized amplitude values for the remaining electrodes 26. In the case where significant dorsal-ventral migration of the neurostimulation leads 12 is determined, the controller/processor 114 may adjust the global amplitude of the electrical stimulation energy (e.g., increasing the global amplitude if the neurostimulation leads 12 migrate away from the spinal cord, and decreasing the global amplitude if the neurostimulation leads 12 migrate toward the spinal cord).

In one embodiment, the controller/processor 114 reprograms the IPG 14 with the new set of stimulation parameters in an automated manner (i.e., without user input specifically designed to reprogram the IPG 14) when the auto-programming function is invoked. In one embodiment, the controller/processor 114 processes the lead migration and coupling efficiency measurements to determine whether the auto-programming function should be invoked upon operative connection between the IPG 14 and the RC 16, e.g., upon establishing connection between the respective telemetry circuitries 88, 118 of the IPG 14 and RC 16. The controller/processor 114 may thereafter periodically perform these processing functions (e.g., every hour or at predetermined times or days).

In an alternative embodiment, the microcontroller 64 (as the controller/processor) and the memory 70 of the IPG 14, itself may invoke the auto-programming function and reprogram the IPG 14 with the new set of stimulation parameters in an automated manner. In this case, the IPG 14, instead of the RC 16, may conveniently perform all the functions associated with determining whether the auto-programming function should be invoked. In this case, a connection between the IPG 14 and RC 16 is not required.

In an optional embodiment, an alert signal is generated when the auto-programming function is invoked. The alert signal is user-discernible in that the patient can readily be alerted to the fact that at least one of the neurostimulation leads 12 has migrated relative to the baseline position outside of the acceptable lead position tolerance and/or one of the activated electrodes has been deemed inefficient. Preferably, the alert signal is binary, meaning that it only indicates if a particular condition has been satisfied or not satisfied (i.e., at least one of the neurostimulation lead 12 has or has not migrated from the baseline position outside of the acceptable lead position tolerance or all of the activated electrodes 26 are or are not efficient).

In one embodiment, the RC 16 (or alternatively, the external charger 22) can alert the patient upon operative connection between the IPG 14 and the RC 16 (or alternatively, the external charger 22), e.g., upon establishing connection between the respective telemetry circuitries 88, 118 of the IPG 14 and RC 16. In the illustrated embodiment, the controller/processor 114 prompts an indicator (and in this case, the speaker 103) to output the alert signal in the form an aural signal (e.g., distinctive tones, patterns of sounds, music, voice messages, etc.) to the patient. Alternatively, the indicator can be the display 102, in which case, the outputted alert signal can take the form of a visual signal (e.g., a blinking icon). Or, the indicator may be a mechanical transducer (not shown), in which case, the outputted alert signal can take the form of a vibratory signal (e.g., the case 100 can vibrate). Preferably, the controller/processor 114 automatically prompts the indicator to output the alert signal immediately upon invoking the auto-programming function, but alternatively, the processor 114 may prompt the indicator to output the alert signal only upon a user inquiry (e.g., pressing a button (not shown) on the RC 16).

In another embodiment, the IPG 14, itself, can alert the patient without establishing connection with the RC 16. This is especially useful if the IPG 14, rather than the RC 16, invokes the auto-programming function. In the illustrated embodiment, the controller/processor 114 prompts an indicator associated with the IPG 14 to generate the alert signal. Because the IPG 14 is implanted within the patient, the indicator may simply be the electrodes 26 on the neurostimulation leads 12, in which case, the outputted alert signal can take the form of a modulated neurostimulation signal (e.g., pulsing the neurostimulation signal on and off at a frequency less than the pulse frequency (e.g., every three seconds) or repeatedly increasing and decreasing the amplitude of the neurostimulation signal) that can be perceived by the patient as distinguished from normal, operative stimulation used for the therapy.

Rather than automatically reprogramming the IPG 14 with the new set of stimulation parameters upon the invoking the auto-programming function, the RC 16 may provide the user with the option of delivering the neurostimulation energy in accordance with the current set of stimulation parameters or delivering the neurostimulation energy in accordance with the new set of stimulation parameters. In this case, the previously described alert signal may take the form of one or more prompts that are displayed to the user on the display 102 of the RC 16. In one embodiment, the RC 16 first prompts the user to either deliver electrical stimulation energy from the IPG 14 in accordance with the current set of stimulation parameter or in accordance with the new set of stimulation parameters. For example, the RC 16 may instruct the user to actuate one of the buttons on the control pad 104 if the user desires to deliver electrical stimulation energy in accordance with the current set of stimulation parameters, and instruct the user to actuate another one of the buttons on the control pad 104 if the user desires to deliver electrical stimulation energy in accordance with the new set of stimulation parameters. The user can toggle the delivery of the electrical stimulation energy back and forth between the current set of stimulation parameters and the new set of stimulation parameters to ascertain whether reprogramming of the IPG 14 with the new set of stimulation parameters will improve therapy in view of the lead migration. The RC 16 may then instruct the user to actuate still another one of the buttons on the control pad 104 if the user desired to reprogram the IPG 14 with the new set of stimulation parameters.

Although the lead migration and electrode efficiency processing, stimulation parameter generation, and reprogramming steps have been described as being performed either by the controller/processor 114 of the RC 16 or the microcontroller 64 of the IPG 14, it should be noted that these steps can be split between the controller/processor 114 and microcontroller 64. For example, the magnitude of lead migration and/or electrode coupling efficiency can be determined by the microcontroller 64 and the auto-programming function can be invoked by the controller/processor 114. Furthermore, although the auto-programming technique has been described with respect to the RC 16, it should be appreciated that the auto-programming technique can be alternatively or additionally be performed by the CP 18.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:
1. A neurostimulation system, comprising:
    an implantable device connected to at least two implantable neurostimulation leads, the implantable device including a neurostimulator configured to deliver, using a first set of stimulation parameters, electrical energy through the neurostimulation leads to spinal cord tissue; and an external device configured to communicate with the implantable device, wherein the neurostimulation system includes:
  monitoring circuitry configured to monitor migration between the leads and monitor migration of at least one of the leads with respect to the spinal cord tissue; and
  at least one controller/processor configured to communicate with the monitoring circuitry, to use the monitored migration between the leads, the monitored migration of at least one of the leads with respect to the spinal cord tissue, and at least one threshold value to determine when lead migration is significant, and to generate, when lead migration is determined to be significant, a second set of stimulation parameters using the monitored migration between the leads and the monitored migration of at least one of the leads with respect to the spinal cord tissue,
  wherein the neurostimulator is configured to use the first set of stimulation parameters to stimulate a virtual multipole defining a volume of activation relative to the spinal cord tissue, and to use the second set of stimulation parameters, which was generated using the monitored migration between the leads and the monitored migration of at least one of the leads with respect to the spinal cord tissue, to stimulate the virtual multipole wherein the second set of stimulation parameters include fractionalized amplitude values that emulate the virtual multipole.

2. The neurostimulation system of claim 1, wherein each lead has electrodes, and the monitoring circuitry is configured to deliver an electrical signal between the electrodes, measure an electrical parameter in response to delivering the electrical signal, and use the measured electrical parameter to monitor migration between leads.

3. The neurostimulation system of claim 2, wherein the measured electrical parameter includes impedance.

4. The neurostimulation system of claim 2, wherein the measured electrical parameter includes a field potential.

5. The neurostimulation system of claim 2, wherein the monitoring circuitry is configured to generate an electric field and monitor for a deviation in voltage caused by action potentials in the target tissue induced by the electric field.

6. The neurostimulation system of claim 1, wherein at least one of the leads has an optical transducer and the monitoring circuitry is configured to send an optical signal from the optical transducer to the target tissue, measure a return signal from the target tissue and use the return signal to monitor the migration with respect to the target tissue.

7. The neurostimulation system of claim 1, wherein at least one of the leads has an ultrasound transducer and the monitoring circuitry is configured to send an ultrasound signal from the ultrasound transducer to the target tissue, measure a return signal from the target tissue, and use the return signal to monitor the migration with respect to the target tissue.

8. The neurostimulation system of claim 1, wherein the at least one controller/processor is configured to automatically reprogram the neurostimulator with the second set of stimulation parameters when lead migration is determined to be significant.

9. The neurostimulation system of claim 1, further comprising an external control device configured to generate an alert signal when the lead migration is determined to be significant, and to reprogram the neurostimulator with the second set of stimulation parameters in response to a user input.

10. The neurostimulation system of claim 1, wherein the monitoring circuitry is configured to sense coupling efficiency with the target tissue and use the sensed coupling efficiency to monitor the migration with respect to the target tissue.

11. The neurostimulation system of claim 1, wherein the leads are configured to be implanted in an epidural space to deliver electrical energy to the spinal cord tissue.

12. The neurostimulation system of claim 11, wherein the monitoring circuitry is configured to monitor migration between the leads to monitor rostro-caudal migration along the spinal cord.

13. The neurostimulation system of claim 11, wherein the monitoring circuitry is configured to monitor migration between the leads to monitor medio-lateral migration transverse to the spinal cord.

14. The neurostimulation system of claim 11, wherein the monitoring circuitry is configured to monitor migration of at least one of the leads with respect to the target tissue to monitor dorsal-ventral migration relative to the spinal cord.

15. The neurostimulation system of claim 1, wherein the external device includes both the monitoring circuitry and the at least one controller/processor.

16. The neurostimulation system of claim 1, wherein the implantable device includes both the monitoring circuitry and the at least one controller/processor.

17. The neurostimulation system of claim 1, wherein the implantable device includes the monitoring circuitry and the external device includes the at least one controller/processor.

18. A method, comprising:
  delivering, using a first set of stimulation parameters, electrical energy through neurostimulation leads to stimulate a virtual multipole defining a volume of activation relative to spinal cord tissue;
  monitoring migration between the neurostimulation leads;
  monitoring migration of at least one of the leads with respect to the spinal cord tissue;
  using at least one controller/processor to use the monitored migration between the leads, the monitored migration of at least one of the leads with respect to the spinal cord tissue, and at least one threshold value to determine when lead migration is significant, and generate, when lead migration is determined to be significant, a second set of stimulation parameters using the monitored migration between the leads and the monitored migration of at least one of the leads with respect to the spinal cord tissue; and
  delivering, using the second set of stimulation parameters which was generated using the monitored migration between the leads and the monitored migration of at least one of the leads with respect to the spinal cord tissue, electrical energy through neurostimulation leads to stimulate the virtual multipole defining the volume of activation relative to the spinal cord tissue, wherein the second set of stimulation parameters include fractionalized amplitude values that emulate the virtual multipole.

19. The method of claim 18, further comprising:
  automatically reprogramming a neurostimulator to stimulate the virtual multipole defining the volume of activation with the second set of stimulation parameters when lead migration is determined to be significant; or
  generating an alert signal using an external control device when the lead migration is determined to be significant; and reprogramming a neurostimulator to stimulate the virtual multipole defining the volume of activation with the second set of stimulation parameters in response to a user input.

20. A non-transitory machine-readable medium including instructions, which when operated on by a machine, cause the machine to perform a method including:
- deliver, using a first set of stimulation parameters, electrical energy through neurostimulation leads to stimulate a virtual multipole defining a volume of activation relative to spinal cord tissue;
- monitor migration between the neurostimulation leads;
- monitor migration of at least one of the leads with respect to the spinal cord tissue;
- use the monitored migration between the leads; the monitored migration of at least one of the leads with respect to the spinal cord tissue, and at least one threshold value to determine when lead migration is significant, and generate, when lead migration is determined to be significant, a second set of stimulation parameters using the monitored migration between the leads and the monitored migration of at least one of the leads with respect to the spinal cord tissue; and
- deliver, using the second set of stimulation parameters which was generated using the monitored migration between the leads and the monitored migration of at least one of the leads with respect to the spinal cord tissue, electrical energy through neurostimulation leads to stimulate the virtual multipole defining the volume of activation relative to the spinal cord tissue, wherein the second set of stimulation parameters include fractionalized amplitude values that emulate the virtual multipole.

* * * * *